(12) United States Patent
Smith et al.

(10) Patent No.: US 7,179,928 B2
(45) Date of Patent: Feb. 20, 2007

(54) SYNTHESIS OF TRIPHENYLPHOSPHONIUM QUINOLS AND QUINONES

(75) Inventors: Robin Andrew James Smith, Dunedin (NZ); Michael Patrick Murphy, Cambridge (GB)

(73) Assignee: Antipodean Pharmaceuticals, Inc., San Francisco, CA (US)

( * ) Notice: Subject to any disclaimer, the term of this patent is extended or adjusted under 35 U.S.C. 154(b) by 150 days.

(21) Appl. No.: 10/486,797

(22) PCT Filed: Aug. 12, 2002

(86) PCT No.: PCT/NZ02/00154

§ 371 (c)(1),
(2), (4) Date: Oct. 1, 2004

(87) PCT Pub. No.: WO03/016323

PCT Pub. Date: Feb. 27, 2003

(65) Prior Publication Data

US 2005/0043553 A1 Feb. 24, 2005

(30) Foreign Application Priority Data

Aug. 13, 2001 (NZ) .................................. 513547

(51) Int. Cl.
*C07C 50/04* (2006.01)
*C07C 50/06* (2006.01)
(52) U.S. Cl. .......................... 552/303; 568/9
(58) Field of Classification Search ................ 552/303; 568/9
See application file for complete search history.

(56) References Cited

FOREIGN PATENT DOCUMENTS

| | | |
|---|---|---|
| EP | 0 289 223 A1 | 11/1988 |
| JP | 59-39855 | 3/1984 |
| JP | 7-223991 | 8/1995 |
| JP | 8-239340 | 9/1996 |

OTHER PUBLICATIONS

Coulter et al., Mitochondrially targeted antioxidants and thiol Reagents, Free Radical Biology & Medicine (2000), 28(10), 1547-1554.*
Kelso et al., Selective Targeting of a Redox-active Ubiquinone to Mitochondria within Cells, J. Biol. Chem., Feb. 2001; 276: 4588-4596.*
Coulter, C., et al., "Mitochondrially Targeted Antioxidants and Thiol Reagents," *Free Radic Biol Med.*, 28(10):1547-54, May 15, 2000.
Goto, G., et al., "A Facile Synthesis of 1,4-Benzoquinones Having a Hydroxyalkyl Side Chain," *Chem Pharm Bull* (Tokyo), 33(10):4422-31, 1985.
Kelso, G., et al., "Selective Targeting of a Redo-Active Ubiquinone to Mitochondria within Cells," *J. Biol. Chem.*, 276(7):4588-4596, Feb. 16, 2001.
Okamoto, K., et al., "Synthesis of quinones having carboxy- and hydroxy-alkyl side chains, and their effects on rat-liver lysosomal membrane," *Chem Pharm Bull* (Tokyo). Aug. 1982; 30(8):2797-819.

* cited by examiner

*Primary Examiner*—Thurman K Page
*Assistant Examiner*—Chukwuma Nwaonicha
(74) *Attorney, Agent, or Firm*—Seed IP Law Group PLLC

(57) ABSTRACT

The methods of preparing quinols and quinones typified by mitoquinol and mitoquinone where a compound typified by idebenone is reacted with $Ph_3PHX$ and $Ph_3P$, where X is a halogen atom.

9 Claims, No Drawings

SYNTHESIS OF TRIPHENYLPHOSPHONIUM QUINOLS AND QUINONES

This is a nationalization of PCT/NZ02/00154 filed Aug. 12, 2002 and published in English.

The present invention relates to the synthesis of triphenyl phosphonium quinols and quinones such as mitoquinol and mitoquinone.

In the Journal of Biological Chemistry, Vol. 276, No. 7, 16 Feb. 2001, pp 4588–4596, Kelso et al. *"Selective Targeting of a Redox-active Ubiquinone to Mitochondria within Cells"* there is disclosed a utility for mitoquinol as a targeted antioxidant for use in the mitochondria of cells, a method of synthesis of mitoquinol and the oxidative changes of mitoquinol to mitoquinone. See also U.S. Pat. No. 6,331,532.

The full content of that publication is hereby here included by way of reference.

Mitoquinol has the following structure

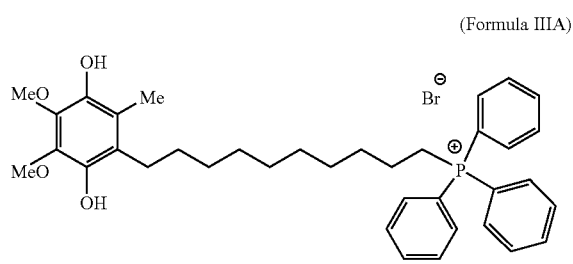
(Formula IIIA)

Its oxidised form is mitoquinone which has the structure

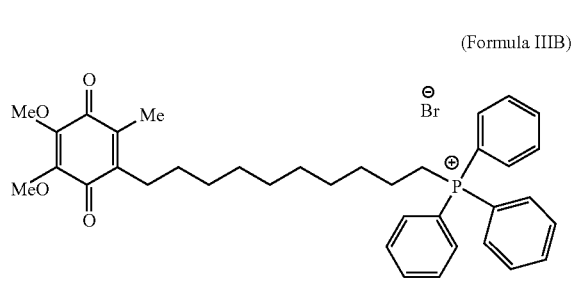
(Formula IIIB)

The present invention relates (in a preferred form) to an alternative synthesis of mitoquinol, mitoquinone, or mixtures of mitoquinol and mitoquinone. It also relates more generally to the synthesis of similar carbon chain linked triphenyl phosphonium and quinol and/or quinone compounds.

In one aspect the present invention consists in a method of synthesis of a compound with a moiety or the moiety of the formula

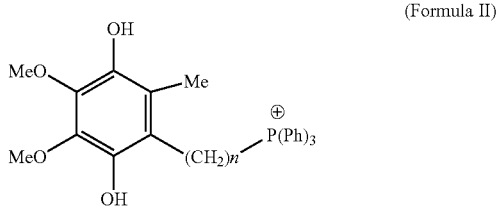
(Formula II)

(and/or its quinone form) where n is an integer from at least 2 (preferably at least 6) to 40 which comprises or includes the reaction of a compound of the formula

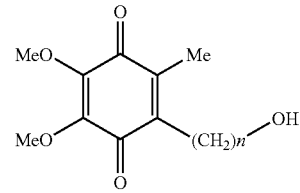

(and/or its quinol form) in the presence of Ph$_3$PHX and Ph$_3$P, where X is a halogen atom.

Preferably X is preferably bromine, iodine or chlorine (most preferably bromine).

Whilst n can be from 2 upwards drop for the reaction where n is less than 6 sufficiently to render alternative synthesises more economic.

Preferably n is 6 to 25.

Preferably the reaction is maintained as a temperature below which significant amounts of MePPh$_3$ are not formed by ether cleavage, eg; the mixture is preferably kept below 80° C.

In still another aspect the present invention consists in a method of synthesis of a compound with a moiety or the moiety of the formula

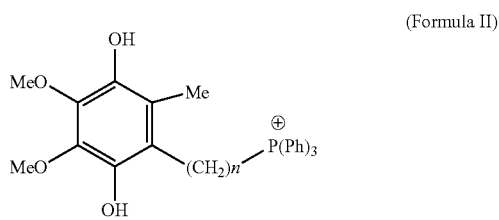
(Formula II)

(and/or its quinone form) where n is an integer from 6 to 40 which comprises or includes the preparation or obtaining of a compound of formula

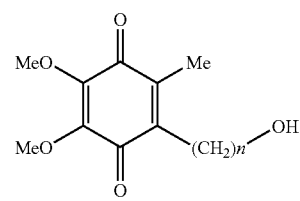

(and/or its quinol form) and its subsequent reaction in the presence of Ph$_3$PHBr and Ph$_3$P.

Preferably n is from 6 to 25.

Preferably the reaction is maintained as a temperature below which significant amounts of MePPh$_3$ are not formed by ether cleavage, eg; the mixture is preferably kept below 80° C.

By a procedure as follows the starting compounds of Formula 1 where n is from 6 to 40 can be prepared as follows:

(Formula 1)

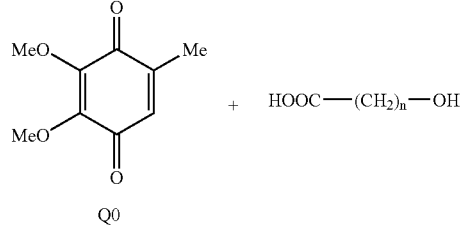

Yields are 30–40% for n=5, 10, 15, 23 and are based on the readily available starting material (Q₀) and the hydroxy-acids—which are well described in the literature.

The method is an adaptation of the procedure in JP 08239340 and gives a ready source of the starting materials.

Other approaches to compounds of Formula 1 are by Friedel-Crafts acylation reaction of trimethoxytoluene followed by two reduction steps and quinone formation as described in JP 07223991, EP 0289223. Chemical and Pharmaceutical Bulletin 33(10), 4422–31 1985, JP 59039855, Chemical and Pharmaceutical Bulletin 30(8), 2797–819 1982.

Idebenone is a compound of Formula 1 but when n=10.

We have determined that idebenone when reacted with $Ph_3PHBr$ will provide the quinol bromide and $Ph_3PO$. Yet when $Ph_3P$ is also present in addition the $Ph_3PHBr$ a pathway exists directly through to mitoquinol.

The present invention therefore in one aspect is a method of synthesis of mitoquinol, mitoquinone or mixtures of mitoquinol and mitoquinone which comprises or includes the reaction of idebenone in the presence of $Ph_3PHBr$ and $Ph_3P$.

Idebenone is disclosed in §4932 in The Merck Index, 12$^{th}$ Edition.

Preferably the ratio of the idebenone with the $Ph_3PHBr$, the idebenone with the $Ph_3P$ and the ratio of the $Ph_3PHBr$ with the $Ph_3P$ is substantially stoichiometric.

Preferably the reaction is maintained as a temperature below which significant amounts of $MePPh_3$ are not formed by ether cleavage, eg; the mixture is preferably kept below 80° C.

In the preferred form of the present invention the reaction through to substantially pure mitoquinol can be described by the following procedure:

(Formula IV)

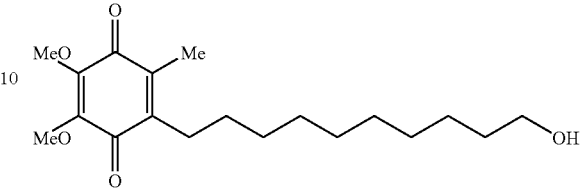

Idebenone $Ph_3PHBr/Ph_3P$ (e.g.; see Example 2)

(Formula IIIA)

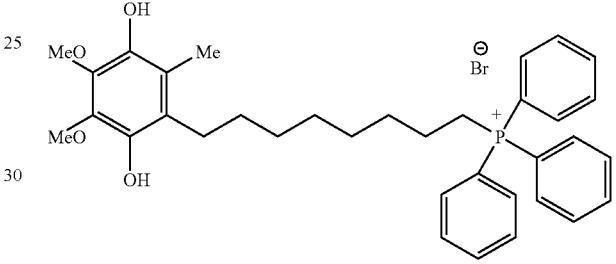

(plus possibly some Mitoquinone) + $Ph_3PO$

PURIFICATION (e.g.; see Example 3) or by vacuum chromatography and filtration)

MITOQUINOL (and/or MITOQUINONE) (Formula IIIA and/or IIIB)

REDUCTION (if needed) (e.g.; using borohydride) MITOQUINOL

Preferably the product that results from the reaction of the idebenone in the presence of the $Ph_3PHBr$ and $Ph_3P$ is mitoquinol (and possibly some of the oxidised species mitoquinone) as well as $Ph_3PO$.

Preferably that reaction product can be purified to substantially purer mitoquinol and/or mixtures of mitoquinol and mitoquinone. For example by washing off with a solvent for $Ph_3PO$ (eg; Et-OAc) and washing with a solvent (eg; $H_2O$ optionally with HBr present) for any phosphonium salts (eg; $MePPh_3$) or by separation by chromatography.

We have found that it is possible to isolate the material by the procedure hereinafter described by reference to both Example 2 and Example 3 and/or 4.

It will be seen that we have found that it is possible with simple EtOAc washing until all of the $Ph_3PO$ has been removed and thereafter a simple water wash (with a presence of HBr) to remove the $MePPh_3$ (albeit with some loss of the target material) provides purity levels desired, ie; a minimum of 98% mitoquinol (if any mitoquinone present, it is also considered as mitoquinol).

Alternatively a vacuum chromatography/filtration is possible.

If subsequently needed any mitoquinone present or at least some of the mitoquinone present can be reduced through to the mitoquinol form (eg; using a borohydride).

The present invention also consists in mitoquinol and/or mitoquinone synthesised by any part of a procedure as hereindescribed (including as a precursor or as part of such synthesis of $Ph_3PHBr$ preparation typified by Example 1).

We have determined we can carry out the following reaction for n being 6 and above (eg; to 40):

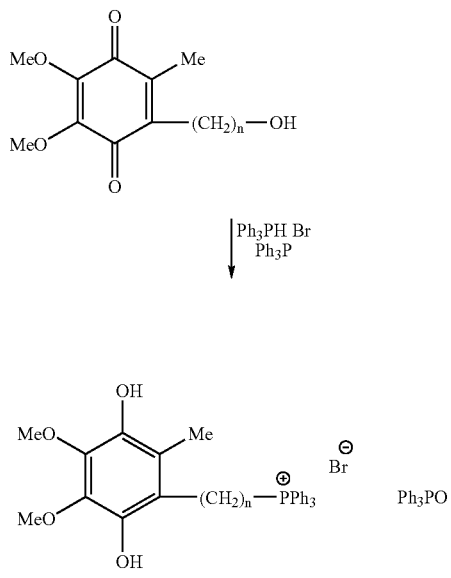

Yields were low however (eg; for n=3, n=5) when n was below 6.

The present invention will now be further described by reference to the following Examples:

EXAMPLE 1

$Ph_3PHBr$ Preparation $Ph_3P$ (39.3 g, 0.15 mol) was added to 48% aq. HBr (105 mL). The solution was stirred at 70° C. for 5 minutes, cooled and extracted with $CHCl_3$ (3 45 ml).

The combined organic phase was dried over $Na2SO_4$, filtered and the solvent was removed in vacuo.

The residue was washed with warm EtOAc (90 ml); yield: 36.6 g (71%). (Hercouet, A., Le Corre, M. Synthesis, 157 (1988))

EXAMPLE 2

Mitoquinol Preparation

Idebenone (0.678 g, 2 mmol, Sequoia Research Products # SRP00400i), $Ph_3P$ (0.524 g, 2 mmol) and $Ph_3PHBr$(0.686 g, 2 mmol) were placed in a 120×16 mm KIMAX tube fitted with a screw cap together with a small TEFLON™ coated spin bar. The tube was flushed with nitrogen, sealed and the bottom 2 cm was placed in a 70° C. oil bath on a magnetic stirrer/hotplate with stirring of the mixture. The solids melted quickly to give an easily stirred orange liquid. As the reaction proceeded the mixture became very viscous and turned dark red/brown.

Progress of the reaction was monitored by removing a small sample and recording the $^{31}P$ NMR in $CDCl_3$: $PPh_3$/ $PHPh_3Br$ −4.7 ppm, $PPh_3$=O 30.2 ppm, $PPh_3Me$ 23.0 ppm and the product had a peak at 25.6 ppm.

After 16 hours some of the starting materials were still evident but after 22 hours the reaction was complete.

The mixture was then cooled to give a black, glass-like solid which was dissolved in $CH_2Cl_2$(4 mL), transferred to a RB flask and the solvent evaporated in vacuo to give a dark red oil (2.446 g).

EXAMPLE 3

Purification of MitoQuinol

The residue from the mitoQuinol preparation of Example 2 (2.446 g) was mixed with EtOAc (20 ml) and held at 70° C. for 5 minutes then cooled and the solvents decanted. This process was repeated twice more, by which time $^{31}P$ NMR showed no $Ph_3PO$ remained in the solid residue (1.120 g).

The residue (1.120 g) was then washed with a solution of $H_2O$ (20 ml) and 48% HBr (3 drops) at 60° C. for 10 minutes. Any remaining solvent was removed from the residue by evaporation in vacuo (0.5 mm) to give an orange foam (0.763 g, 57%). $^1H$ NMR (299.9 MHz) 7.6–7.9 (m, 15H, —P$^+$Ph$_3$), 3.88 (s, 6H,2' —OCH$_3$), 3.8–3.9 (m, 2H, —CH$_2$—P$^+$Ph$_3$), 2.5—2.6(t, 2H, ubiquinol —CH$_2$—), 2.14 (s, 3H, CH$_3$). $^{31}P$ NMR (121.4 MHz) 25.7 ppm.

EXAMPLE 4

Purification of MitoQuinol

The residue (216 g, 0.326 mol) from the EtOAc washing of the crude reaction material (64% -ol, 20% -one, 16% $MePPh_3Br$) as in the first part of Example 3 was dried in vacuo then dissolved in methanol (700 mL). A solution of 30% aqueous $H_2O_2$ (70 mL, 0.618 mol) and pyridine (134 mL) were added and the mixture was stirred 21 hrs at room temperature. The methanol was then evaporated in vacuo and the crude mixture was dissolved in dichloromethane (1.6 L) and extracted with 2% aqueous HBr (4×700 mL). The organic layer was dried over $MgSO_4$ and added directly to a silica gel bed (1.2 kg (Merck type 9385) dry packed, 65 mm deep by 245/230 mm wide in a sintered glass funnel). The silica gel was washed using a slight vacuum with dichloromethane (1.0 L), then 5% rectified spirits in dichloromethane (10.0 L) and 10% rectified spirits in dichloromethane (3.0 L).

Evaporation of the 5% rectified spirits in dichloromethane solution gave of pure mitoQuinone (166.2 g, 76.9%). $^1$H NMR (299.9 MHz) 7.7–7.9 (m, 15H, —P$^+$Ph$_3$), 3.98 (s, 6H, 2× —OCH$_3$), 3.85–3.95 (m, 2H, —CH$_2$—P$^+$Ph$_3$), 2.40 (t, J=7.8 Hz, 2H, ubiquinone—CH$_2$—), 2.00 (s, 3H, CH$_3$). $^{31}$P NMR (121.4 MHz) 25.7 ppm.

Evaporation of the 10% rectified spirits in dichloromethane solution gave a 29:71 mixture of mitoQuinone and methyltriphenylphosphonium bromide (19.2 g).

MitoQuinone (0.31 g, 0.47 mmol) was dissolved in methanol (10 ml) and stirred under argon at room temperature. Sodium borohydride (0.1 g) was added to the stirred solution which went light yellow and the mixture was stirred for 30 minutes. A solution of 48% HBr was then added dropwise until gas evolution finished and the methanol was then evaporated in vacuo. The residue was dissolved in a mixture of dichloromethane (5 ml) and H$_2$O (5 ml) and the organic layer was collected. The aqueous phase was extracted with a further portion of dichloromethane (5 ml). The combined organic fractions were dried over Na$_2$SO$_4$ and the solvents evaporated in vacuo to give a yellow foam (0.305 g, 97%). $^1$H NMR showed no evidence for a peak at 2.045 ppm indicating <3% residual mitoQuinone impurity.

What is claimed is:

1. A method of synthesizing a compound of formula II:

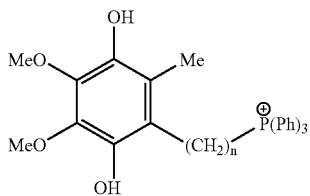

wherein n is an integer from 6 to 40 and where the compound of formula II is present in its quinol form or its quinone form or a mixture thereof, which method comprises:

reacting a compound of formula 1:

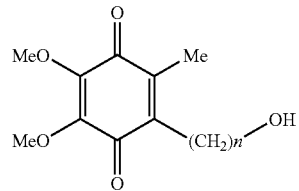

where n is an integer from 6 to 40 and where the compound of formula 1 is present in its quinone form or its quinol form or a mixture thereof, with Ph$_3$PHX and Ph$_3$P, where X is a halogen atom selected from Br, I, and Cl, at a temperature of below 80° C., to obtain the compound of formula II.

2. The method of claims 1 wherein X is Br.

3. The method of claim 1 wherein n is an interger from 6 to 25.

4. The method of claim 1 wherein n is 10.

5. The method of claim 1 wherein prior to the step of reacting, (i) the compound of formula 1, (ii) Ph$_3$P and (iii) Ph$_3$PHX are substantially stoichiometric.

6. The method of claim 1 wherein the compound of Formula 1 is present in its quinone form.

7. The method of claim 1 wherein the compound Formula II is present in its quinol form.

8. The method of claim 1 which further comprises a purification step comprising purifying the compound of formula II.

9. The method of claim 1 which further comprises reducing the quinone form of the compound of formula II to its quinol form.

* * * * *

UNITED STATES PATENT AND TRADEMARK OFFICE
CERTIFICATE OF CORRECTION

PATENT NO.         : 7,179,928 B2                                      Page 1 of 1
APPLICATION NO.    : 10/486797
DATED              : February 20, 2007
INVENTOR(S)        : Smith et al.

It is certified that error appears in the above-identified patent and that said Letters Patent is hereby corrected as shown below:

Title Page;

References Cited (56)
U.S. Patent Documents, --6,331,532, 12/18/01, Murphy et al.-- has been omitted from the issued patent.

Column 8
Line 19, "C., to" should read as --C, to--.

Column 8
Line 40, Claim 7 in the Amendment filed August 30, 2006, --The method of claim 5 wherein X is Br.-- has been omitted from the issued patent. Please add this claim to column 8 as claim number 10.

Signed and Sealed this

Fifth Day of May, 2009

JOHN DOLL
*Acting Director of the United States Patent and Trademark Office*